US012588848B2

(12) United States Patent
Tran et al.

(10) Patent No.: US 12,588,848 B2
(45) Date of Patent: Mar. 31, 2026

(54) DEVICES AND SYSTEMS FOR MEASURING MAGNETIC FIELDS

(71) Applicants: INSTITUT NATIONAL DE LA SANTE ET DE LA RECHERCHE MEDICALE, Paris (FR); CENTRE NATIONAL DE LA RECHERCHE SCIENTIFIQUE, Paris (FR); UNIVERSITE DE MONTPELLIER, Montpellier (FR); CHU MONTPELLIER, Montpellier (FR); EV-TECHNOLOGIES, Colombelles (FR)

(72) Inventors: Quang Hung Tran, Colombelles (FR); Férial Terki, Montpellier (FR); Trung Kien Nguyen, Montpellier (FR); Gudrun Boge, Montpellier (FR); Sidina Wane, Colombelles (FR); Azzedine Bousseksou, Toulouse (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); UNIVERSITE DE MONTPELLIER, Montpellier (FR); CHU MONTPELLIER, Montpellier (FR); EV-TECHNOLOGIES, Colombelles (FR)

( * ) Notice: Subject to any disclaimer, the term of this patent is extended or adjusted under 35 U.S.C. 154(b) by 83 days.

(21) Appl. No.: 18/698,987

(22) PCT Filed: Oct. 10, 2022

(86) PCT No.: PCT/EP2022/078126
§ 371 (c)(1),
(2) Date: Apr. 5, 2024

(87) PCT Pub. No.: WO2023/061952
PCT Pub. Date: Apr. 20, 2023

(65) Prior Publication Data
US 2024/0407693 A1    Dec. 12, 2024

(30) Foreign Application Priority Data
Oct. 11, 2021    (EP) ..................................... 21306423

(51) Int. Cl.
  *A61B 5/243*       (2021.01)
  *A61B 5/00*        (2006.01)
  *G01N 27/82*       (2006.01)

(52) U.S. Cl.
  CPC ............ *A61B 5/243* (2021.01); *A61B 5/0022* (2013.01); *A61B 5/7203* (2013.01);
  (Continued)

(58) Field of Classification Search
  CPC .... A61B 2560/0214; A61B 2562/0223; A61B 2562/182; A61B 5/0022; A61B 5/026;
  (Continued)

(56) References Cited

U.S. PATENT DOCUMENTS

2004/0264090 A1 * 12/2004 Strahm .................. H02H 9/025
                                                            361/93.1
2007/0139040 A1    6/2007 Jones et al.
                (Continued)

FOREIGN PATENT DOCUMENTS

EP           2 685 271 B1     9/2018

*Primary Examiner* — Mark D Remaly
(74) *Attorney, Agent, or Firm* — WCF IP

(57)          ABSTRACT
The invention relates to a measurement device for measuring weak magnetic fields, such as fields in the sub-picotesla range (e.g. lower than a few nanotesla). The measurement device comprises ultrasensitive magnetic sensors (or arrays
(Continued)

of ultrasensitive magnetic sensors) coupled to low-noise processing circuitry. The processing circuitry comprises a two-stage design including low-noise amplifiers and analog filters. The invention is suitable for magnetocardiovascular (MCV) applications thanks to its ability to measure very small magnetic fields with good accuracy and very little noise.

19 Claims, 8 Drawing Sheets

(52) U.S. Cl.
CPC ............ *A61B 5/7225* (2013.01); *A61B 5/725* (2013.01); *G01N 27/82* (2013.01); *A61B 2560/0214* (2013.01); *A61B 2562/0223* (2013.01); *A61B 2562/182* (2013.01)

(58) Field of Classification Search
CPC ..... A61B 5/243; A61B 5/7203; A61B 5/7225; A61B 5/725; G01N 27/82; G01R 33/0029; G01R 33/07; G01R 33/09
See application file for complete search history.

(56) References Cited

U.S. PATENT DOCUMENTS

| | | | |
|---|---|---|---|
| 2011/0152703 A1 | 6/2011 | Zuckerman et al. | |
| 2015/0176964 A1 | 6/2015 | Uberti et al. | |
| 2017/0059667 A1* | 3/2017 | Bassoli | G01C 17/38 |
| 2022/0006813 A1* | 1/2022 | Jorasch | G16H 50/30 |

* cited by examiner a)

b)

DEVICES AND SYSTEMS FOR MEASURING MAGNETIC FIELDS

TECHNICAL FIELD

The present invention relates to the measurement of magnetic fields and signals.

BACKGROUND

Magnetocardiography has recently emerged as a promising technique for analyzing and monitoring cardiovascular systems in live subjects.

This non-invasive technique is based on the measurement of magnetic fields and signals generated by the electrical activity of the heart, for example by electrical currents flowing within myocardial fibers during cardiac activity.

However, such magnetic fields are usually weak (for example, lower than a few nanoTesla) and are thus hard to measure accurately.

Measurement devices based on superconducting sensors, such as SQUID (Superconducting QUantum Interference Devices) magnetometers have been proposed, as such sensors are very sensitive and are capable of measuring weak magnetic fields with enough precision.

However, these SQUID-based systems are often cumbersome to use, as they require constant cooling, among other reasons.

There is therefore a need for magnetic measurements systems for measuring small magnetic fields, especially for medical applications such as magnetocardiography, capable of overcoming the drawbacks associated with existing measurement systems, such as SQUID-based measurement systems. In addition, such system is also promising for measurement of small quantity of magnetic materials such as magnetic nanoparticles or for non-destructive detection of small crack in ferrous metal materials.

SUMMARY

An object of the present invention is therefore to provide a measurement device for measuring magnetic signals, comprising:

a magnetic sensor, and an electronic processing circuit connected to an output of the magnetic sensor, the electronic processing circuit comprising:

a first amplifier and filter stage, connected in series with the output the magnetic sensor, a second amplifier and filter stage, connected in series with the first amplifier and filter stage, and an analog to digital converter connected to an output of the second amplifier and filter stage, the magnetic sensor being a high sensitivity magnetoresistance sensor having high thermal stability, the first amplifier and filter stage comprising a first low noise amplifier and at least a first linear analog and/or a first non-linear analog filter, the second filter stage comprising a second low noise amplifier and a second linear analog filter and a second non-linear analog filter, the analog-to-digital converter being further connected to an output interface of the processing circuit.

According to advantageous optional aspects, alternative embodiments of the invention may comprise one or more of the following features, taken alone or according to all possible technical combinations:

the first amplifier and filter stage comprises a first low noise amplifier and a first linear analog filter, the second amplifier and filter stage comprises a second low noise amplifier and a second non-linear analog filter;

the second linear filter comprises a Butterworth band pass filter, the filter having preferentially a frequency range from 0.01 Hz to 1000 Hz;

the first and second non-linear analog filters are used to eliminate frequency components of 50 Hz or 60 Hz and/or their harmonics;

the magnetic sensor and the electronic processing circuit are integrated on a same substrate, such as an embedded application-specific integrated circuit system on a chip or an embedded system in a package;

the measurement device further comprises an integrated low noise power supply, the low noise power supply comprising at least:

an electrical battery for supplying electric power to the low noise amplifiers, to the linear analog filter and to the non-linear analog filter, and a power conversion module comprising a low noise current limiter for supplying electric power, at least, to the magnetic sensor, the power conversion module being configured to be powered by an external power source;

the measurement device further comprises an electromagnetic shielding structure encasing the magnetic sensor and the electronic processing circuit, for example made of mu-metal and/or comprising a Faraday cage;

a measurement system comprising a measuring device as briefly described above and a processor, such as a programmable microcontroller, connected to an output of the electronic processing circuit is configured to implement digital filters comprising at least: a linear filter, a non-linear filter, and a Kalman filter;

a measurement system comprising a computer system and a device for measuring magnetic signals, the computer system is connected to an output of the measurement device, and wherein the computer system is configured to implement digital filters comprising at least: a linear filter, a non-linear filter, and a Kalman filter;

the computer system is connected to the measurement device by a high-speed data link;

the high-speed data link is a wired high-speed data link, such as an Ethernet connection, or a wireless high-speed over the air data link, such as a 5G telephone network connection;

the measurement system comprises a built-in self-test function configured to monitor the functionality of the magnetic sensor and to allow calibration of the sensitivity of the magnetic sensor, the measurement system is configured to measure magnetic fields created by the cardiovascular system of a living subject and/or by electrical activity of a living subject and/or vascular network of living entities, the magnetic sensor is a sensor matrix configured to measure, either in series or in parallel, the magnetic field generated from a part of the vascular network of a living subject, with a spatial resolution comprised between 0.1 µm and 10 mm;

the measurement system is configured to extract of at least one of the following data for examining the condition of the vascular system of a subject:

flow direction of at least a portion of the vascular system, such as a blood vessel or a plurality of blood vessels, pulsation rate, pulsatility index and resistance index of at least a portion of the vascular system, capacitance of wall compliance of at least a portion of the vascular system, Inductance of blood flow of at least a portion of the vascular system, pressure of at least a portion of the vascular system, velocity of blood flow in at least a portion of the vascular system, velocity of pulse wave propagation of at least a portion of the vascular system stiffness of at least a portion of the vascular wall.

the measurement system is configured to measure the presence of magnetic field originate from magnetic materials or to measure magnetic properties of small quantity of magnetic materials, such as ferrous metal or magnetic nanoparticles or spin-crossover materials.

the measurement system is configured to employ in non-destructive detection of cracks or thickness reduction in walls containing ferrous compounds and/or magnetic impurities such as oil or gas pipelines, oil and gas tankers or any architectures of oil or gas containers.

BRIEF DESCRIPTION OF THE DRAWINGS

The invention will be understood upon reading the following description, provided solely as an example, and made in reference to the appended drawings, in which.

DESCRIPTION OF SOME EMBODIMENTS

Figure 1:
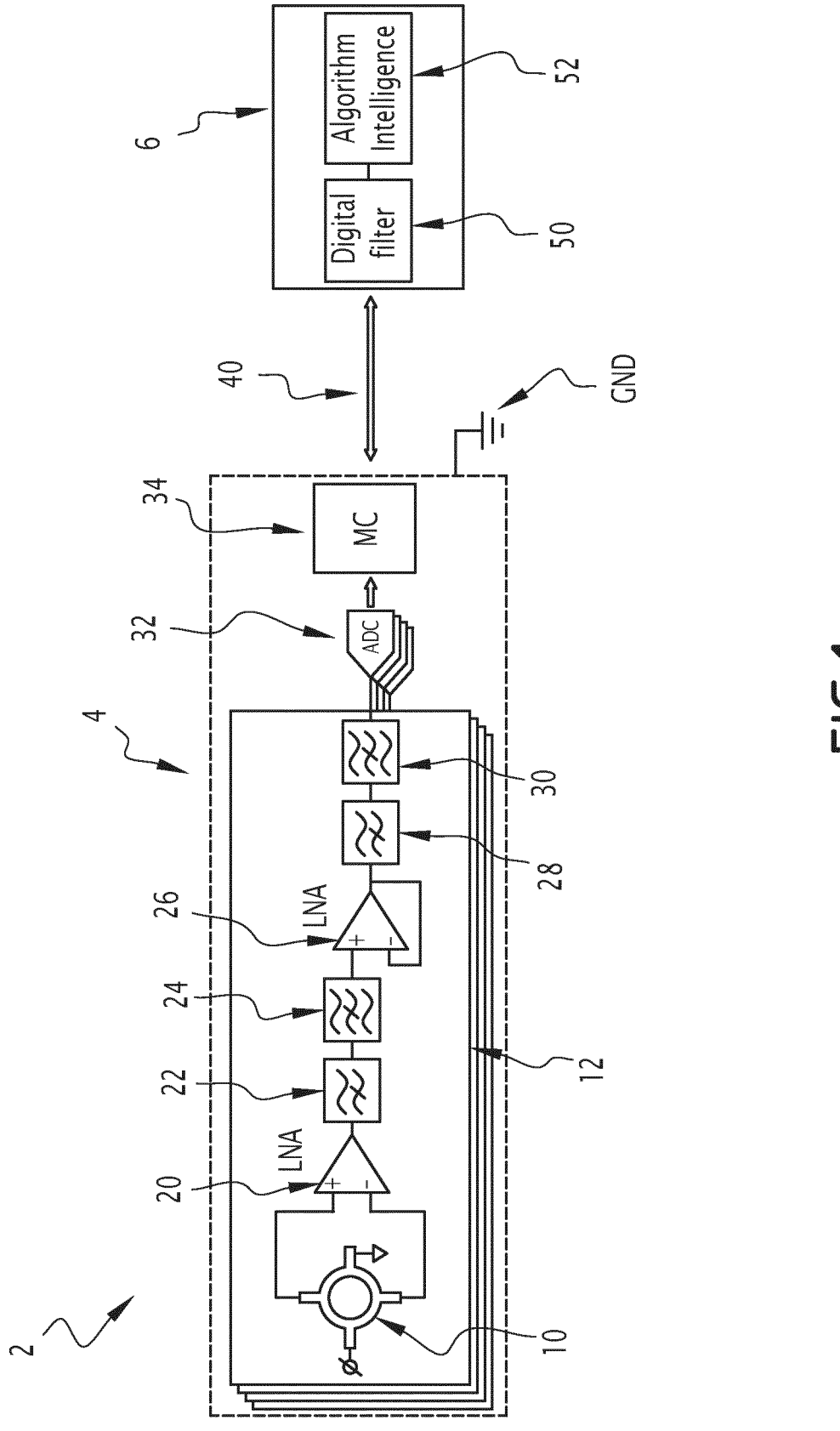
FIG. 1 is a schematic diagram of a measurement system for measuring magnetic fields, the measurement system comprising a device for measuring magnetic signals according to embodiments of the invention.
Figure 2:
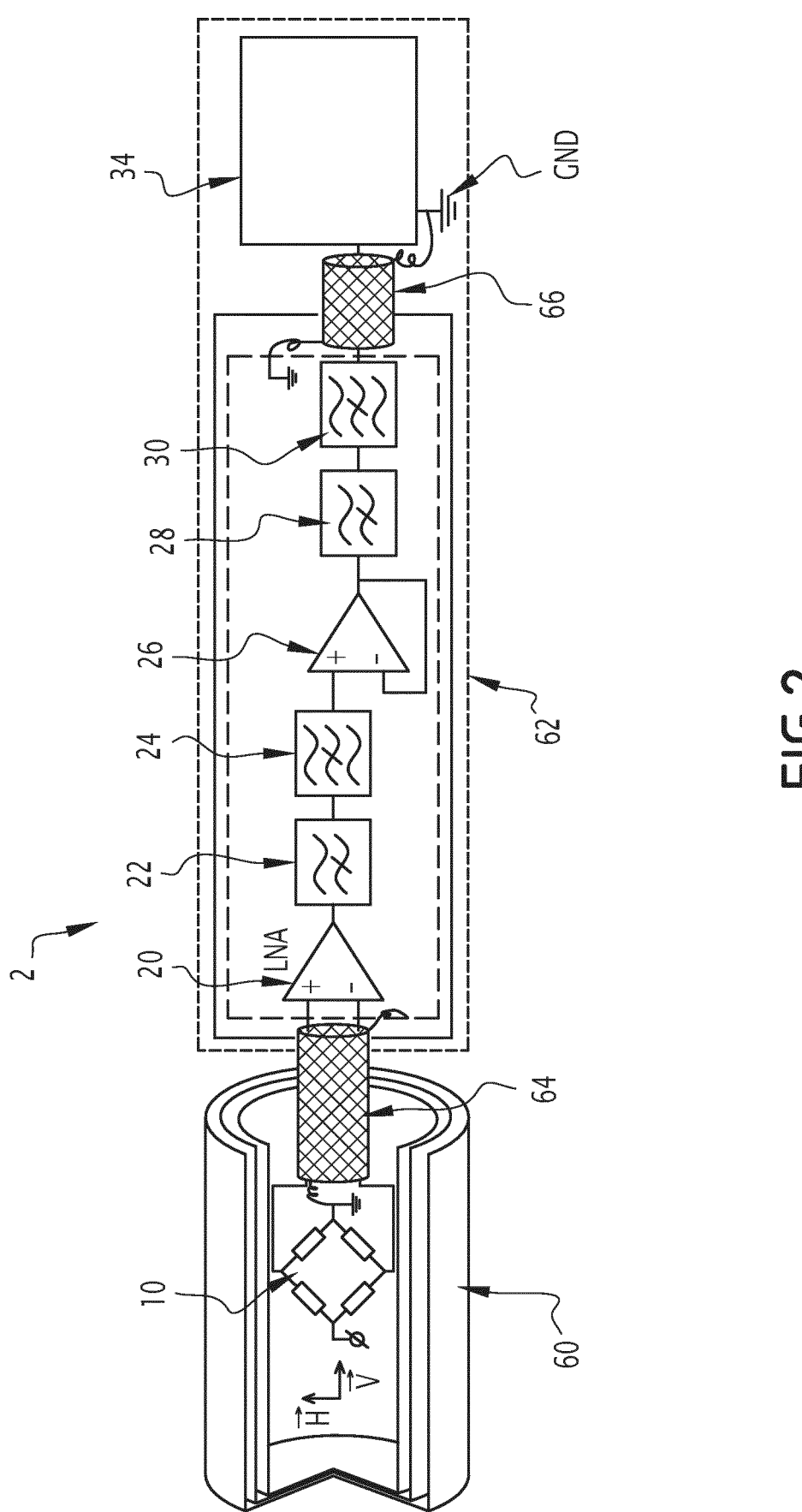
FIG. 2 is a schematic diagram of the measurement system of FIG. 1, in which electromagnetic shielding elements have been made visible.

FIGS. 1 and 2 illustrate a measurement system 2 for measuring magnetic fields.

Preferably, the measurement system 2 is configured to measure magnetic fields created by the cardiovascular system of a living subject, such as a human patient, although many other applications are possible.

The measurement system 2 comprises a device 4 for measuring magnetic signals and a computer system 6 connected to the measurement device 4.

The measurement device 4 comprises a magnetic sensor 10, and an electronic processing circuit 12 connected to an output of the magnetic sensor 10.

In preferred embodiments, the magnetic sensor 10 comprises a high sensitivity magnetoresistance sensor. For example, the magnetic sensor 10 is a planar Hall effect magnetic sensor.

In some embodiments, the magnetic sensor 10 may comprise one or more sensing elements. Each sensing element includes a multilayer structure of magnetic thin films structured in order to form a microstructure having a specific shape.

In the illustrated example, the microstructure has a central circular shape comprising four identical or similar radial arms regularly spaced around the central circular shape and extending outwards of the central circular shape.

The sensing element(s) may be connected to electrical contact pads, for allowing a wired connection with the electronic processing circuit 12.

For example, the magnetic sensor 10 comprises a first output terminal and a second output terminal. The magnetic sensor is configured to deliver an output signal, such as a voltage, between the first output terminal and the second output terminal.

In a non-limiting example given for illustrative purposes, the magnetic materials stack may include an exchange biased multilayer structure of Ta/Py/Cu/IrMn/Ta layers (Permalloy, Copper, Iridium-Manganese alloy as well as Tantalum buffer layers), each layer having a thickness lower than 10 nanometers.

This multilayer structure may be annealed during fabrication at high temperature under a uniform magnetic field in order to increase temperature stability of the magnetic properties of the multilayer structure.

This shape and materials can create magnetoresistance properties and/or planar Hall effect properties, which are used by the sensor to detect magnetic fields.

An example of this magnetic sensor is described in the international application WO 2017/207640 A1, the contents of which being incorporated by reference in the present application.

On FIG. 2, the arrows V and H illustrate respectively the direction of the biasing voltage applied to the sensor and the magnetic field sensibility direction during some measurements. The biasing voltage V can be applied between a biasing voltage input and a ground input (respectively visible as the leftmost electrode and the rightmost electrode of the magnetic sensor 10 on FIGS. 1 and 2).

For example, the magnetic sensor 10 has a high sensitivity of higher than 10 V/T.

In many embodiments, the magnetic sensor 10 is a high sensitivity magnetoresistance sensor having high thermal stability with a variation of below ten part per million per degree Celsius (ppm/° C.).

Preferably, the magnetic sensor 10 has a small size.

For example, the smallest size of the sensing element is smaller than 50 μm and preferably smaller or equal to 10 μm. In the illustrated example, the magnetic sensor 10 fits a dicing area of 2×2 mm². Other embodiments are nonetheless possible.

The electronic processing circuit 12 is more particularly designed to rapidly and efficiently process the signals measured by the magnetic sensors 10 (e.g. to filter and amplify the signals) while preserving a good signal to noise ratio. This is important, as the signals representing the very weak magnetic fields measured by the magnetic sensor 10 are so weak that they can be easily drowned by noise.

For example, in a vascular network, the magnetic field is on the range from picoTesla to nanoTesla.

For example, the electronic processing circuit 12 is a low noise processing circuit.

In many embodiments, the electronic processing circuit 12 comprises a first amplifier and filter stage (or "first stage", comprising elements 20, 22 and 24), a second amplifier and filter stage (or "second stage", comprising elements 26, 28 and 30).

The first stage and the second stage are connected in series with the output of the magnetic sensor 10. More precisely, the first stage is connected to the output of the magnetic sensor 10. The second stage is connected to the output of the first stage.

The electronic processing circuit 12 also comprises an analog to digital converter 32 connected to an output of the second filter stage.

The first stage comprises a first low noise amplifier (LNA) 20, and at least a linear analog filter 22 and/or a non-linear 24 analog filter. The first linear analog filter 22 is configured to filter out continuous parasitic components of the signal such as the signature of the terrestrial magnetic field.

In this example, the first stage comprises a first linear analog filter 22 and a first non-linear analog filter 24, connected together in series at the output of the first low noise amplifier 20.

In an illustrative example, the first low noise amplifier 20 has a nominal noise of 0.25 nV $Hz^{-1/2}$ and a fixed gain of 2000.

In a non-limiting example given for illustrative purposes, the first linear analog filter 22 is a 0.01 Hz high-pass filter configured to remove the DC offset component.

According to an embodiment, the first linear analog filter 22 is a Butterworth filter having preferentially a frequency range from 0.01 Hz to 1000 Hz.

The first non-linear analog filter 24 may be a 50 or 60 Hz non-linear filter configured to remove the noises from the electrical network (since the measurement system 2 may be at least partially powered by the electrical network grid having a main frequency of 50 Hz or 60 Hz) and more generally to further eliminate peaks attenuation of 50 Hz or 60 Hz and/or their harmonics.

The second stage comprises a second low noise amplifier 26 and at least a second linear analog filter 28 and/or a second non-linear analog filter 30. Preferably, the second stage comprises at least both a second low noise amplifier 26 and a linear analog filter 28.

In this example, the second stage comprises a second linear analog filter 28 and a second non-linear analog filter 30, connected together in series at the output of the second low noise amplifier 26.

For example, the second linear analog filter 28 is a 150 Hz low-pass Butterworth filter, for example with selectable filtering orders from 1 to 3. In other embodiments, the second linear analog filter 28 is a Butterworth filter having preferentially a frequency range from 0.01 Hz to 1000 Hz The second non-linear analog filter 30 may be a 50/60 Hz filter, such as a notch filter, configured to remove the DC offset component and noises from the electrical network, and more generally to further eliminate peaks attenuation of 50 Hz/or 60 Hz and/or their harmonics.

In a non-limiting example given for illustrative purposes, the second low noise amplifier 26 has a nominal noise of 3 nV $Hz^{-1/2}$ and gain of 90.

In another non-limiting example given for illustrative purposes, the second low noise amplifier 26 has a nominal noise of 3 nV $Hz^{-1/2}$ and gain of 180.

The analog-to-digital converter 32 is further connected to an output interface of the processing circuit 12. In this example, analog-to-digital converter 32 is a four channel, 16 bits analog-to-digital converter, other embodiments being nonetheless possible.

For example, the processing circuit 12 comprises a processor 34, such as a programmable microcontroller (MC).

As used herein, the term "processor" refers not only to electronic controller devices including a processor or a microprocessor, but also to other equivalent elements such as application-specific integrated (ASIC) circuits, field-programmable gate array (FGPA) circuits, logic circuits, analog circuitry, equivalents thereof, and any other circuit or processor capable of executing the functions described herein.

The processor 34 may be coupled to a communications interface configured to be coupled to the computer system 6, as will be explained below. The processor 34 may be part of the communications interface.

Preferably, the measurement device 4 is connected to the computer system 6 by a high-speed data link 40. The communications interface is adapted in consequence.

In some embodiments, the high-speed data link 40 is a wired high-speed data link, such as an Ethernet connection. For example, the processor 34 is a 32-bit microcontroller implementing a high-speed Ethernet data transmission protocol.

In some embodiments, the high-speed data link 40 is a wireless over the air high-speed data link, such as a 5G telephone network connection.

In optional but nevertheless advantageous embodiments, the measurement device 4 further comprises an integrated low noise power supply, and a power conversion module.

The low noise power supply comprises at least an electrical battery for supplying electric power to the low noise amplifiers 20 and 26, to the linear analog filter 22, and to the linear analog filter 28.

The power conversion module comprises a low noise current limiter for supplying electric power, at least, to the magnetic sensor 10. The power conversion module may be configured to be powered by an external power source, such as an electrical mains grid.

In preferred embodiments, the magnetic sensor 10 and the electronic processing circuit 12 are integrated on a same substrate. For example, the substrate is a printed circuit board. Other configurations are nevertheless possible in alternative embodiments.

For example, the magnetic sensor 10 may be integrated in an application-specific integrated circuit (ASIC) embedded in a system on a chip (SoC) system, or in an application-specific integrated circuit (ASIC) embedded in a package (SiP).

The magnetic sensor element can be implemented in advanced CMOS Silicon-based technologies taking benefit of most recent packaging solutions (such as Fan-in/Fan-Out Wafer Level Chip Scale Package (WLCSP) and Semiconductor Embedded in Substrate (SESUB) or any appropriate technology).

As shown on FIG. 2, in preferred embodiments, the measurement device 4 further comprises an electromagnetic shielding structure encasing the magnetic sensor and the electronic processing circuit.

The electromagnetic shielding structure is configured to protect the measurement device 4 from high frequency and low frequency noises from ambient environment.

For example, a first portion 60 of the electromagnetic shielding structure surrounds a first portion of the measurement device 4 comprising the magnetic sensor 10.

A second portion 62 of the electromagnetic shielding structure surrounds a second portion of the measurement device 4 comprising the electronic processing circuit 12.

According to some embodiments, the electromagnetic shielding structure is made of mu-metal.

In some other embodiments, the electromagnetic shielding structure comprises a Faraday cage.

Shielded connectors 64 and 66 may be used, respectively, to protect the wired connectors used to connect the magnetic sensor 10 to the electronic processing circuit 12, and to connect the electronic processing circuit 12 to the processor 34. The shielded connectors 64 and/or 66 may be connected to an electrical ground GND of the measurement device 4. Preferably, the shielded connectors 64 and/or 66 are low loss cables.

Additionally, in order to minimize the interference noise from the high-speed data processing by the processor 34 to the analog signals, the electronic processing circuit 12 may be built by following specific design considerations, such as shielding all signal lines or having different ground planes for the analog and digital portions of the electronic processing circuit 12. On FIG. 2, the electrical ground is represented by the symbol GND.

The computer system 6 is configured to further analyze and filter the acquired signals in order to eliminate noise. The computer system 6, also called control system, comprises electronic circuitry capable of executing algorithms and software code.

For example, the computer system 6 may comprise a processor and one or more computer memory elements.

The computer memory stores computer code and/or executable instructions for causing the processor and the electronic control unit to execute a method for processing the received measurement signals when the computer code and/or executable instructions are executed by the processor.

In some embodiments, the computer system 6 may also be configured to control the operation of the ultrasound emission system.

The computer system 6 comprises a communications interface capable of being coupled to and exchanging data with the communications interface of the electronic processing circuit 12.

The computer system 6 may further include a user interface. The user interface may comprise one or more interface elements, such as a graphical display, a wireless interface to allow remote control and/or exchange of data with a mobile terminal, data input means such as a keyboard, a mouse, a pointer device, a touch-sensitive screen, or any equivalent interface element, or any combination of such interface elements.

In preferred embodiments, the computer system 6 comprises a digital filter module 50 and a digital algorithm module 52.

For example, the digital filter module 50 of the computer system 6 is configured to implement digital filters comprising at least: a linear filter, a non-linear filter, for example a notch filter, in order to improve noise reduction.

The digital filters are implemented by filtering algorithms including high-pass, low-pass and notch filters. The algorithms may be Butterworth filters.

For example, the low pass digital filter may be the following low-pass Butterworth filter to cut off the input voltage, $V_{in}(j\omega)$, having frequency higher than the cut-off frequency value $\omega_c$:

$$\left| V_{out,LP}^n(j\omega) \right| = V_{in}(j\omega) \frac{1}{\sqrt{1 + \left(\frac{\omega}{\omega_c}\right)^{2n}}}$$

The high pass digital filter may be the following high-pass Butterworth filter for cutting off voltage signal with frequency lower than the expected value:

$$\left| V_{out,HP}^n(j\omega) \right| = V_{in}(j\omega) \frac{1}{\sqrt{1 + \left(\frac{\omega_c}{\omega}\right)^{2n}}}$$

The notch filter may be the following notch Butterworth filter, used to remove unwanted noises at established frequency values, for example noises from electrical power 50/60 Hz and their harmonics:

$$\left| V_{out,Notch}^n(j\omega) \right| = V_{in}(j\omega) \frac{1}{\sqrt{1 + \left(\frac{\omega W}{\omega^2 - \omega_c^2}\right)^{2n}}}$$

In these equations, $\omega$ is the angular frequency ($\omega = 2\pi f$, f: frequency at the measured time), $\omega_c$ is the angular frequency at cut-off value (f=$f_c$), W is the angular frequency at cut-off bandwidth, and n is the number of filter orders, j being the imaginary number.

By increasing the number of filter orders, the filter quality is increased.

The module 52 is configured to implement one or more advanced digital filters, the aim being to further extracting useful information from the filtered digital signals.

This is particularly useful in medical applications, such as with magnetocardiovascular system, in which automatic classifiers may be used to provide clinical conclusions and/or automated diagnosis based on the collected signals.

For example, the module 52 may be configured to implement a Kalman filter in order to remove unwanted noise signals and to generate a clean signal capable of being used in automated diagnosis systems.

However, in some embodiments, the processor 34 may be configured to implement said digital filters comprising at least: a linear filter, a non-linear filter, and a Kalman filter, for example in cases where the computer system 6 is not connected to the measurement device 4.

According to an embodiment, the filters implemented by module 50 are adaptive, in other words their parameters are automatically updated to adapt to the application. The updated parameters are for example the cutoff frequency and cutoff bandwidth of notch filter; cutoff frequency, bandwidth and orders of low-pass and high-pass filters.

Similarly, according to an embodiment module 52 is configured to implement adaptive advanced filter, for example to learn and update parameters such as the estimated noise and the measurement noise of a Kalman filter.

In conclusion, the measurement system 2 is advantageously capable of measuring low magnetic fields (such as fields or of a few nanoTesla or lower) with a high sensitivity (up to $10^{-15}$ emu), on a wide range of frequencies (e.g., from 10 mHz to 10 GHZ).

This is in large part due to the association of the magnetic sensor 10 with the electronic processing circuit 12 which has been designed so as to match the magnetic sensor 10 and ensure that the measured signals are processed (e.g., amplified, filtered, converted into digital signals) by the electronic processing circuit 12 with as little added noise as possible.

Furthermore, the digital filters implemented by computer 6 or by processor 34 achieve further filtering of the noise to allow a quality filter higher than −105 dB. Advantageously, the analog filters of the first and second stages, and the digital filters cooperate to achieve the desired quality of noise filtering.

The invention is therefore particularly suitable for use in medical applications such as magnetocardiovascular (MCV) applications, as the measurement system has the ability to measure very small magnetic fields with good accuracy and very little noise.

For example, the measurement system 2 is capable of measuring weak magnetic fields, such as fields (lower than a few nanotesla) in the sub-PicoTesla range.

More specifically, the measurement system 2 is capable of reliably measuring weak magnetic fields with a precision comparable to that of existing measurement systems based on superconducting magnetometers, but without the practical drawbacks commonly associated to superconducting magnetometers such as SQUID magnetometers.

With the invention, measurements can be performed at ambient temperature and do not require complex and energy-intensive cooling systems.

Moreover, in contrast to other methods, with the present invention, magnetic measurements can be performed non-invasively, without requiring direct contact with the skin of the patient, and without requiring the use of a contrast agent in the patient's body.

Due to the small size of the magnetic sensor 10, the measurement system 2 can be miniaturized more easily.

Figure 3:
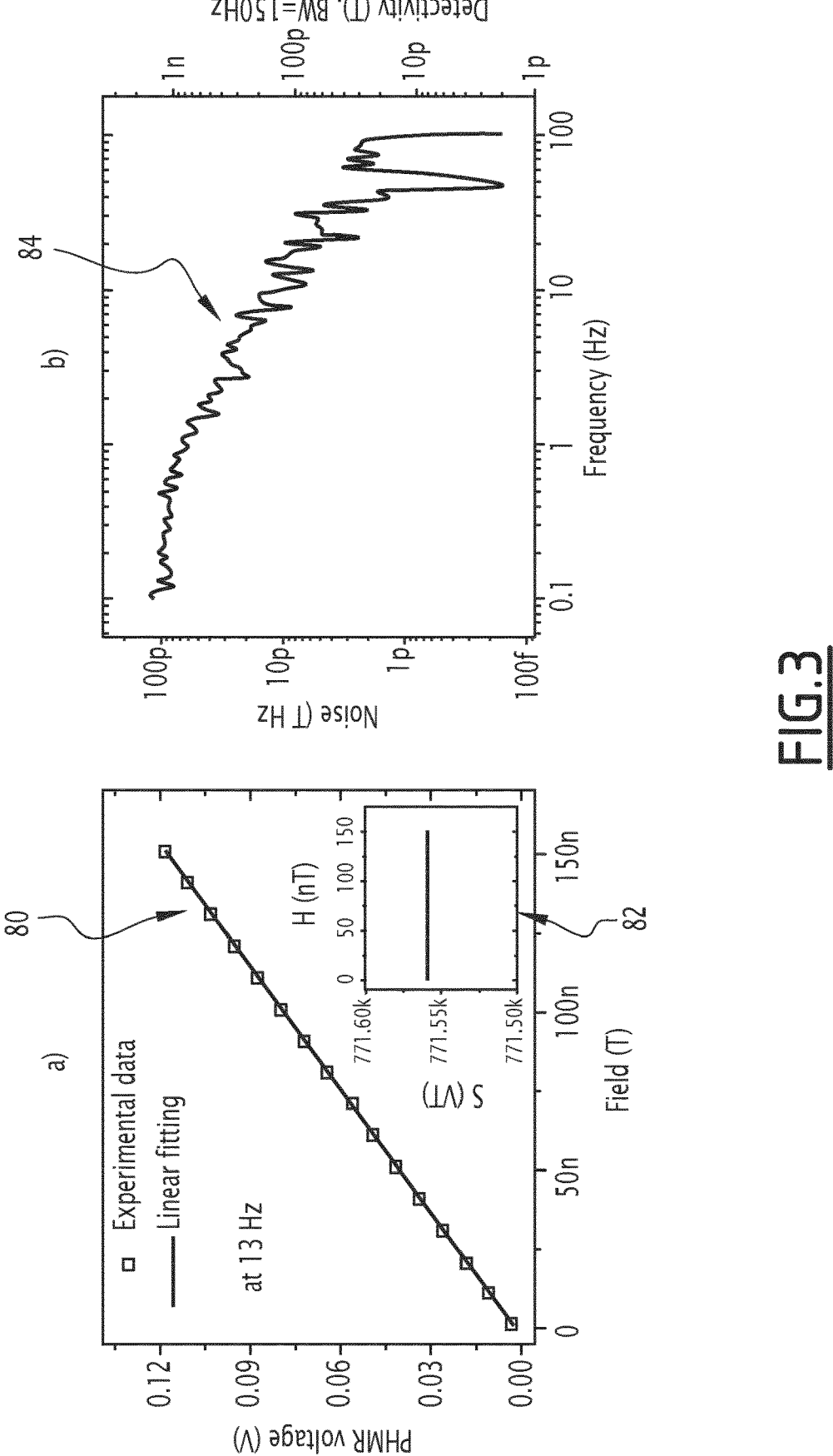
FIG. 3 depicts several graphs illustrating exemplary performance of the measurement system of FIG. 1.

FIG. 3 illustrates exemplary performance of the measurement system.

On the leftmost portion of FIG. 3 (portion a) the first curve 80 illustrates the output voltage response of the measurement device (PHMR voltage, y-axis, in Volts) when increasing or decreasing the magnetic field (x-axis) in the range from 0 nT to 150 nT. In this example, the measurement is performed for a frequency of 13 Hz.

The inset graph corresponds to the estimated sensitivity of the measurement device (curve 82), defined as equal to the derivative of the biasing voltage V over the magnetic excitation field H) and estimated to be equal to circa 771.5 kV/T in this example.

On the rightmost portion of FIG. 3 (portion b), the third curve 84 depicts the evolution of noise (y-axis, expressed as T Hz$^{-1/2}$) as a function of frequency (y-axis). The equivalent magnetic noise floor of the device is estimated to be equal to 100 pT Hz$^{-1/2}$ at 0.1 Hz down to 2 pT Hz$^{-1/2}$ at greater than 100 Hz. The magnetic field detectivity of the system as a function of frequency for the designed frequency bandwidth of 150 Hz can be estimated by the multiplication of the noise level by √150.

Figure 8:
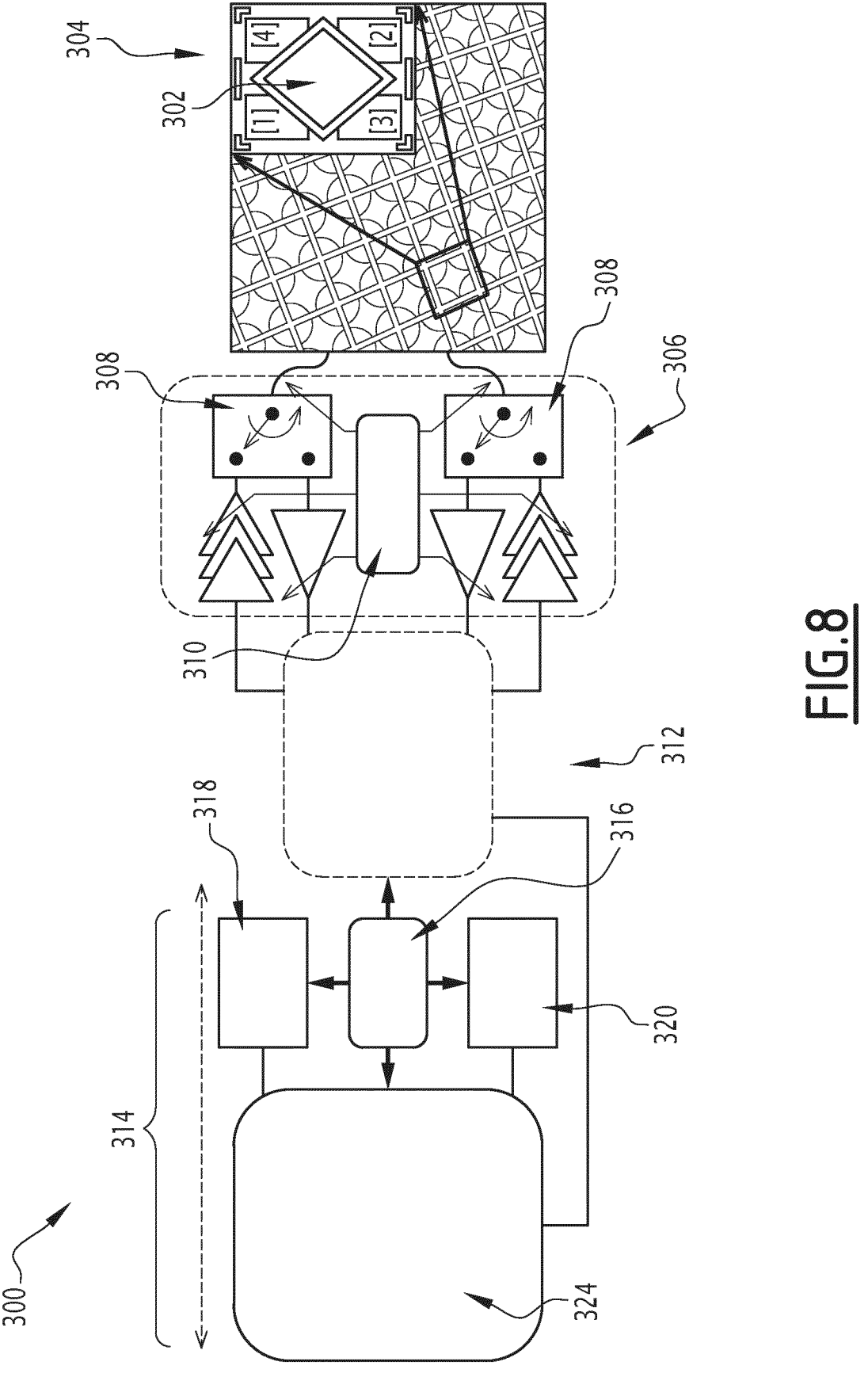
FIG. 8 illustrates a block diagram of an embodiment of the electronic circuitry implementing the measurement system of FIG. 1.

FIG. 8 is a block diagram of an exemplary embodiment of the electronic circuitry used in the measurement device 4, given for illustrative purposes.

In this example, the measurement device 4 is implemented by an application-specific integrated circuit 300 comprising a magnetic sensor similar to the magnetic sensors previously described.

In this example, the magnetic sensor comprises a plurality of magnetic sensor elements 302 arranged to form a sensor array 304.

The sensors array 304 is connected to an analog front-end module (block 306) comprising the filters and amplifier stages previously described.

The analog front-end module 306 comprises switched front-end-modules 308 capable of operating in a transmission mode (TX-Signal Generation) or in a receiver mode (RX).

For example, the magnetic sensor elements 302 are capable of operating in a bidirectional way either in transmission (TX) or in receiver (RX) modes. In the transmission mode, pulsed signals can be generated by the magnetic sensor elements 302 using on-chip oscillators.

The analog front-end module 306 comprises a sensor load-tuning module 310 for broadband impedance matching.

The analog front-end module 306 comprises a built-in self-test function configured to monitor the functionality of the magnetic sensor (i.e. array 304 in the present case) and to allow calibration of the sensitivity of the magnetic sensor.

A signal-conditioning module (block 312) is connected to the output of the analog front-end module 306.

The signal conditioning module 312 is configured to condition the measured signals, for example by filtering the signals. For example, the signal conditioning module 312 may implement a filter-bank and/or the digital filters 50.

The signal conditioning module 312 may be configured for potential down-conversion for base-band processing with sensor calibration. This module 312 may control the biasing and sensitivity adjustments as well.

An advanced signal processing stage 314 is connected to the output of the signal-conditioning module 312.

For example, the signal processing stage 314 is configured to operate at base-band frequency and process all required algorithmic calculations for extracting the needed signals for the final application. The signal processing stage 314 adjusts and coordinates the control and regulation of the sensors, for example using modules 316, 318 and 320.

The signal processing stage 314 includes features (module 324) for implementing of modulation schemes and the communication protocol for high data rate transmissions.

This implementation is preferable to existing solutions based on discrete solutions with separate analog and digital signal processing blocs. Because the measurement system is designed from scratch as an ASIC-based implementation, it is easier to combine analog detection with real-time signal processing while properly taking into account the correlation between noise sources.

Many other embodiments are possible.

Figure 4:
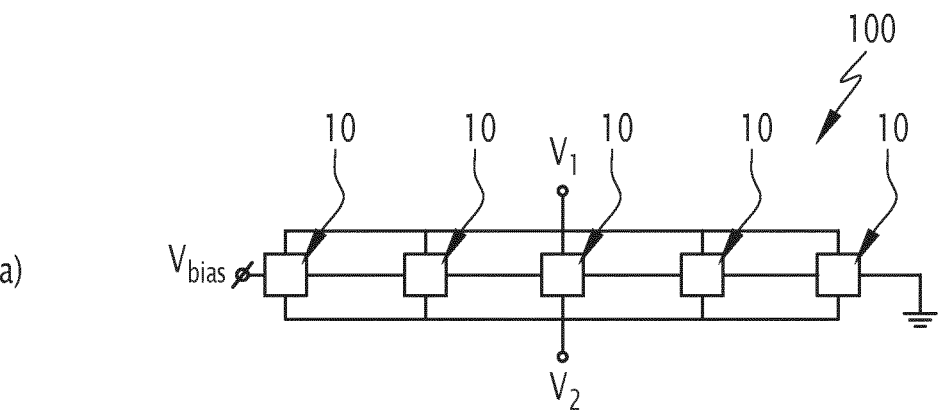
FIG. 4 illustrates first and second embodiments of a magnetic sensor array capable of being used in the measurement system of FIG. 1.
Figure 4:
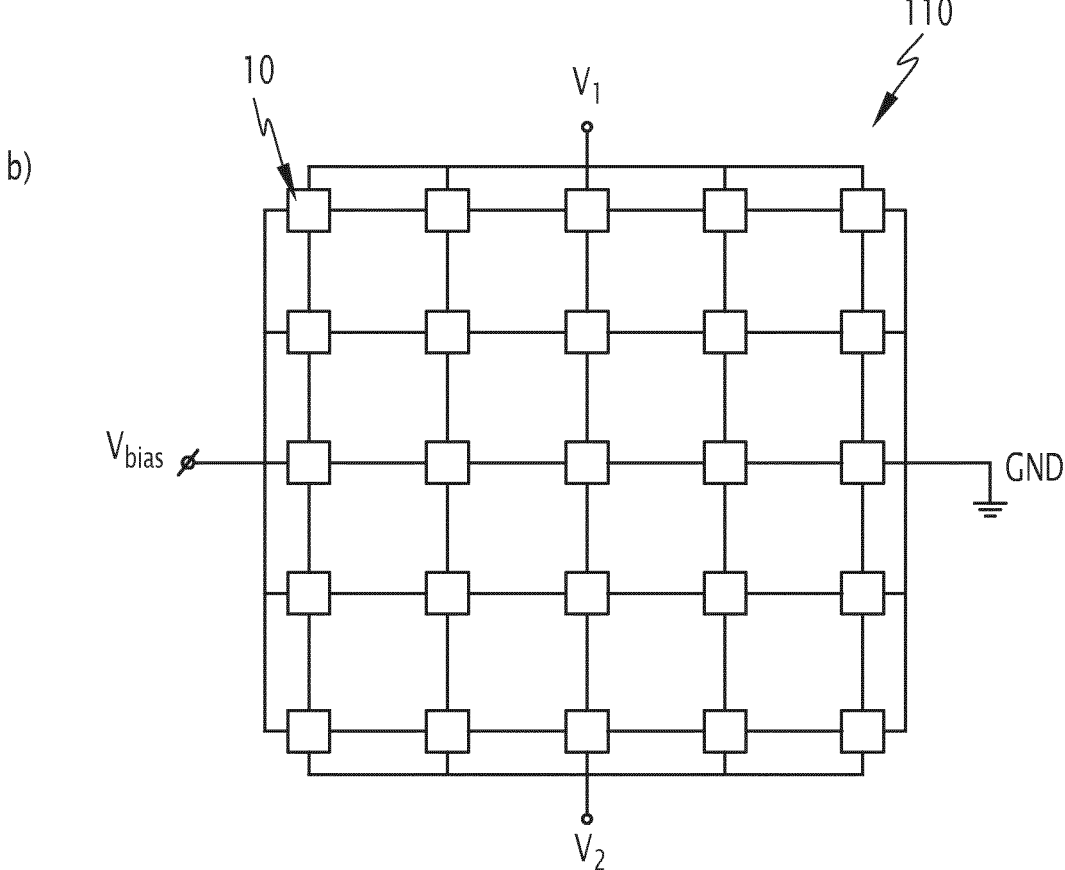
Figure 5:
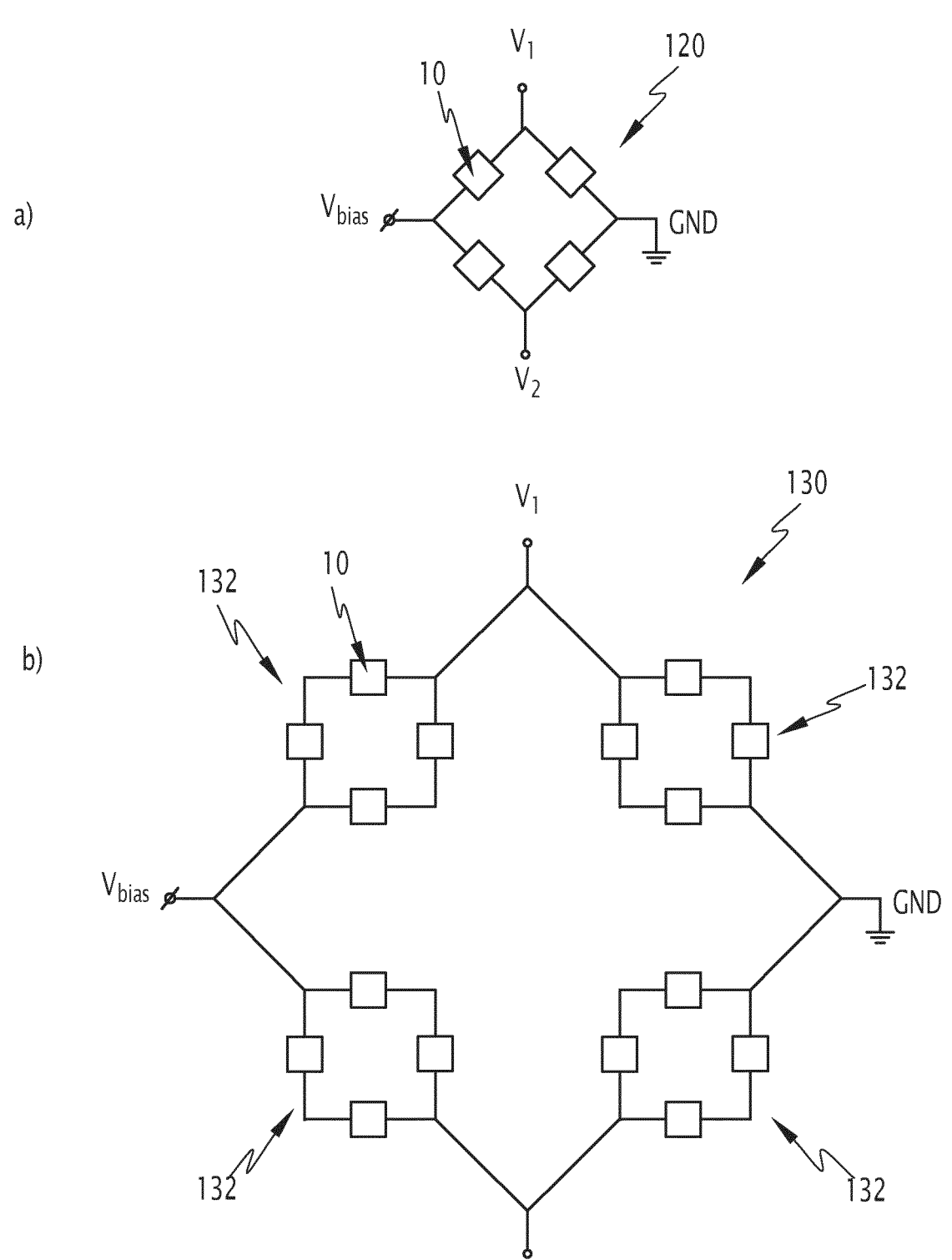
FIG. 5 illustrates third and fourth embodiments of a magnetic sensor array capable of being used in the measurement system of FIG. 1.

FIGS. 4 and 5 illustrate alternative embodiments of the magnetic sensor 10, in which the single magnetic sensor 10 described in reference to the embodiment of FIG. 1 is replaced by a sensor array or by a sensor matrix, in order to perform measurements in a plurality of positions in space.

In the present specification, the expression "magnetic sensor 10" can be used to refer to a single magnetic sensor element as described above, or to a combination of multiple magnetic sensor elements, such as a sensor array or a sensor matrix.

Examples of magnetic sensor arrays or matrices are now described.

FIG. 4 (*a*) illustrates a sensor array 100 comprising a plurality of individual magnetic sensors 10 aligned along a longitudinal direction.

The sensor array 100 allows precise measurements along a defined geometrical direction. For example, the sensors 10 of the sensor array 100 are periodically spaced along the longitudinal direction. Preferably, the individual sensors 10 are identical or at least similar in their properties.

In the illustrated example, five sensors 10 are connected together in the array, this number being given solely as a non-limiting example.

For example, the respective first outputs terminals of each sensor 10 are connected to a main first output V1. The respective second outputs terminals of each sensor 10 are connected to a main second output V2. The sensors 10 are connected in series by their voltage biasing input and their ground input between a main voltage biasing input $V_{bias}$ and a main electrical ground GND.

FIG. 4 (*b*) illustrates a sensor matrix 110 comprising a plurality of individual sensors 10. The sensor matrix 110 is constructed in a way similar to the sensor array 100, except that the sensors 10 are connected to form a pattern along two dimensions, such as a square, instead of a single direction.

The sensor matrix 110 allows precise measurements along two directions.

For example, the sensors 10 of the sensor matrix 110 are periodically spaced along the two longitudinal directions. Preferably, the individual sensors 10 are identical or at least similar in their properties.

The sensors 10 are connected in series by their respective first output terminal and their second output terminal between a main first output V1 and a main second output V2. The sensors 10 are connected in series by their voltage biasing input and their ground input between a main voltage biasing input $V_{bias}$ and a main electrical ground GND.

FIG. 5 (*a*) illustrates a sensor matrix 120 comprising four individual sensors 10 connected in a bridge-like pattern between a main first output V1, a main second output V2 a main voltage biasing input $V_{bias}$ and a main electrical ground GND. The sensors 10 may be connected to said main outputs V1, V2, $V_{bias}$ and GND by their respective first and second outputs.

FIG. 5 (*b*) illustrates a sensor matrix 130 comprising four sensor modules 132 in a bridge-like pattern between a main first output V1, a main second output V2 a main voltage biasing input $V_{bias}$ and a main electrical ground GND. Each sensor module 132 is similar or identical to the sensor matrix 120. The sensors modules 132 may be connected to said main outputs V1, V2, $V_{bias}$ and GND by their respective first and second main outputs (e.g., the main outputs V1 and V2 visible on FIG. 5 (*a*)).

These configurations allow more precise measurements along two directions. Due to the small size of the magnetic sensor 10, the sensor matrix 100, 110, 120 and 130 can be miniaturized for low spatial resolution measurement more easily.

In preferred embodiments, the magnetic sensor 10 is configured to measure, either in series or in parallel, the magnetic field generated from a part of the vascular network of a living subject, with a spatial resolution in a range from 10 mm to micrometer (μm) range or sub-micrometer range, for example down to 1 mm, or 100 μm, or 10 μm, or 1 μm, or 0.1 μm.

For example, the spatial resolution is comprised between 0.1 μm and 10 mm.

In many embodiments, the magnetic sensor 10 is part of a sensing probe.

Some possible applications of the measurement device 4 and of the measurement system 2 are now described by way of example.

For example, the measurement system 2 is configured to extract of at least one of the following information data for examining the conditioning condition of the vascular system of a subject:

flow direction of at least a portion of the vascular system, such as a blood vessel or a plurality of blood vessels, pulsation rate, pulsatility index and resistance index of at least a portion of the vascular system, capacitance of wall compliance of at least a portion of the vascular system, inductance of blood flow of at least a portion of the vascular system, pressure of at least a portion of the vascular system, velocity of blood flow in at least a portion of the vascular system, velocity of pulse wave propagation of at least a portion of the vascular system stiffness of at least a portion of the vascular wall.

Figure 6:
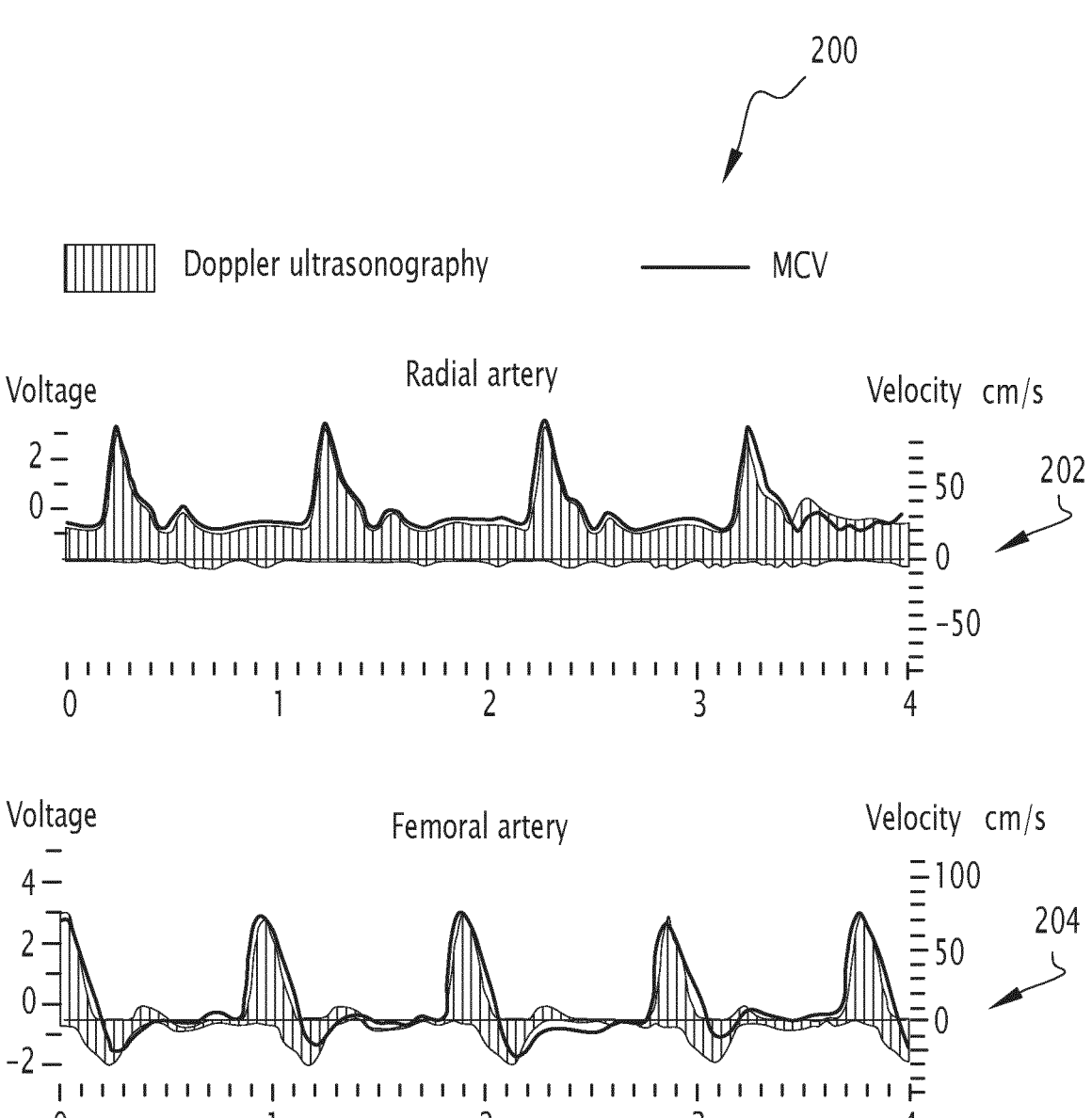
FIG. 6 illustrates a comparison of experimental measurement results of Doppler ultrasonography and a method using the measurement system of FIG. 1.

On FIG. 6, diagrams 200 illustrate results of magnetocardiovascular measurements performed with the measurement system 2 on a radial artery (graph 202) and a femoral artery (graph 204) of a subject (such as a human subject) to determine circulatory impedance/resistance.

In both cases, the measured signals are given as a function of time (x-axis, expressed in arbitrary units) and expressed in a voltage (given as output by the magnetic sensor(s) 10).

The results acquired with the present measurement system 2 (denoted by a continuous line) are shown on both graphs 202 and 204 alongside measurement results obtained with known techniques, such as Doppler ultrasonography (displayed as a dashed area and expressed as a velocity in cm/s).

It can be seen that the data obtained with the measurement system 2 is in good experimental agreement with the reference data obtained from Doppler ultrasonography, meaning that the measurement system 2 can provide magnetocardiovascular data as reliably as known techniques such as Doppler ultrasonography, despite being much simpler to use and implement.

Figure 7:
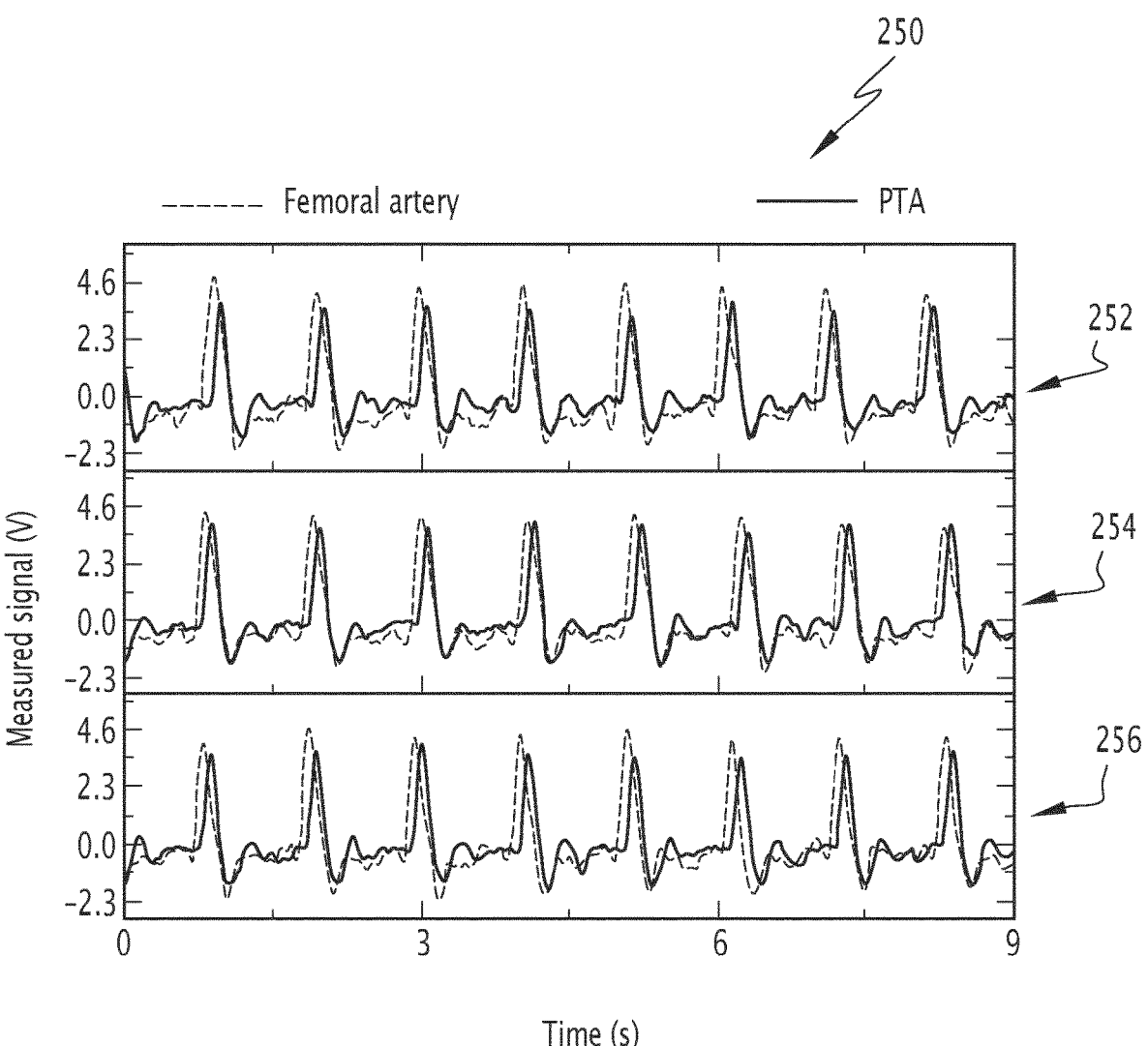
FIG. 7 illustrates another comparison of experimental measurement results of Doppler ultrasonography and a method using the measurement system of FIG. 1.

On FIG. 7, diagrams 250 illustrate results of magnetocardiovascular measurements performed with the measurement system 2 on the lower limb of a human subject, to determine the velocity of pulse wave propagation in the femoral artery.

For example, the arterial wave generated by the systolic ejection of the subject's heart propagates along the aorta and then through the arteries of the vascular system, at a speed that depends on the elasticity of the arterial wall. Thus, measuring this speed gives a reliable information on the elasticity of the arterial walls in at least of a portion of the vascular system of the subject.

The three graphs referenced 252, 254 and 256 correspond to the output of three repeated measurements of two separate points spaced apart and arranged longitudinally along the lower limb.

The magnetocardiovascular data measured with the measurement system 2 from two measurement probes similar in sensitivity and phase in detection of an alternative magnetic signal, are expressed as a voltage ("Measured signal" on the y-axis) as a function of time (x-axis, in seconds) and are represented as solid lines and dotted lines. Solid lines and dotted lines correspond to the two measurements at the posterior tibial artery with the legend "PTA" and at the femoral artery along the lower limb. For example, the data may have been collected using multiple sensors 10 spaced apart from each other, or with a sensor array similar to the sensor array 100 with low spatial resolution.

The magnetocardiovascular data allows to analyze the velocity of pulse wave propagation by dividing the distance of the two measurement points to the time different of the two measurements at the systolic peak. In the measurement example on a healthy volunteer, the velocity of pulse wave propagation at lower limb is around 10 m/s, it is in good agreement with the reference data obtained using known measurement methods, such as the combination of Doppler ultrasound and photoplethysmography (PPG) measurements. The reference data may be obtained with the correlation of two measurements sets of separate Doppler/PPG probes.

The experimental results once again show that the magnetocardiovascular data obtained with the measurement system 2 is in good experimental agreement with the reference data.

This means that the measurement system 2 can be as reliable as reliably as known techniques such as methods based on Doppler ultrasound, despite being much simpler to use and implement.

Many other embodiments are possible. The embodiments and alternatives described above may be combined with each other in order to create new embodiments of the invention, within the scope of the claims.

Advantageously, the measurement device comprises a high sensitivity magnetoresistance sensor with high thermal stability, so as to accurately measure small magnetic fields, for example in the vascular network of a patient.

Advantageously, cascading a first amplifier and filter stage and a second amplifier and filter stage allows overcoming the gain-bandwidth tradeoff of amplifiers.

Advantageously, the electromagnetic shielding structure encasing the magnetic sensor 10 and the electronic processing circuit 12 helps avoiding high frequency and low frequency noises from ambient environment.

The invention was described in its application for the measurement of magnetic fields and signals in the field of magnetocardiography.

The applications of the invention are not limited to this field.

For example, advantageously, the measurement system 2 is configured to measure the presence of magnetic field originating from magnetic materials or to measure the magnetic properties of small quantity of magnetic materials, such as ferrous metal or magnetic nanoparticles or spin-crossover materials.

For example, advantageously, the measurement system 2 is configured for non-destructive detection of cracks or thickness reduction in walls containing ferrous compounds and/or magnetic impurities such as oil or gas pipelines, oil and gas tankers or any architectures of oil or gas containers. Therefore, advantageously, the invention finds applications for monitoring pipeline systems in oil and gas industry

The invention claimed is:

1. A measurement device for measuring magnetic signals, comprising:

only one magnetic sensor, and an electronic processing circuit connected to an output of the magnetic sensor, the electronic processing circuit comprising:

a first amplifier and filter stage, connected in series with the output the magnetic sensor, a second amplifier and filter stage, connected in series with the first amplifier and filter stage, and an analog to digital converter connected to an output of the second amplifier and filter stage, the magnetic sensor being a high sensitivity magnetoresistance sensor having high thermal stability, the first amplifier and filter stage comprising a first low noise amplifier and at least a first linear analog filter configured to filter out parasitic magnetic fields and a first non-linear analog filter, the second amplifier and filter stage comprising a second low noise amplifier and a second linear analog filter and a second non-linear analog filter, the analog-to-digital converter being further connected to an output interface of the processing circuit.

2. The measurement device of claim 1, wherein the first amplifier and filter stage comprises a first low noise amplifier and a first linear analog filter, the second amplifier and filter stage comprises a second low noise amplifier and a second non-linear analog filter.

3. The measurement device according to claim 1, wherein the each of the first and second linear filter comprises a Butterworth band-pass filter, the band-pass filter having preferentially a frequency range from 0.01 Hz to 1000 Hz.

4. The measurement device according to claim 1, wherein the first and second non-linear analog filters are used to eliminate frequency components of 50 Hz or 60 Hz.

5. The measurement device according to claim 4, wherein the first and second non-linear analog filters are further used to eliminate harmonics of the frequency components of 50 Hz or 60 Hz.

6. The measurement device according to claim 1, wherein the magnetic sensor and the electronic processing circuit are integrated on a same substrate, such as an embedded application-specific integrated circuit system on a chip or an embedded system in a package.

7. The measurement device according to claim 1, wherein the measurement device further comprises an integrated low noise power supply, the low noise power supply comprising at least:

an electrical battery for supplying electric power to the low noise amplifiers, to the linear analog filter and to the non-linear analog filter, and a power conversion module comprising a low noise current limiter for supplying electric power, at least, to the magnetic sensor, the power conversion module being configured to be powered by an external power source.

8. The measurement device according to claim 1, wherein the measurement device further comprises an electromagnetic shielding structure encasing the magnetic sensor and the electronic processing circuit.

9. A measurement system comprising a measurement device for measuring magnetic signals according to claim 1, wherein a processor, such as a programmable microcontroller, connected to an output of the electronic processing circuit, is configured to implement digital filters comprising at least: a linear filter, a non-linear filter, and a Kalman filter.

10. A measurement system comprising a computer system and a measurement device for measuring magnetic signals according to claim 1, wherein the computer system is connected to an output of the measurement device, and wherein the computer system is configured to implement digital filters comprising at least: a linear filter, a non-linear filter, and a Kalman filter.

11. The measurement system according to claim 10, wherein the computer system is connected to the measurement device by a high-speed data link.

12. The measurement system according to claim 11, wherein the high-speed data link is a wired high-speed data link, such as an Ethernet connection, or a wireless high-speed over the air data link, such as a 5G telephone network connection.

13. The measurement system according to claim 9, wherein the measurement system comprises a built-in self-test function configured to monitor the functionality of the magnetic sensor and to allow calibration of the sensitivity of the magnetic sensor.

14. The measurement system according to claim 9, wherein the measurement system is configured to measure magnetic fields created by the cardiovascular system of a living subject or by electrical activity of a living subject or vascular network of living entities.

15. The measurement system according to claim 9, wherein the magnetic sensor is a sensor matrix configured to measure, either in series or in parallel, the magnetic field generated from a part of the vascular network of a living subject, with a spatial resolution comprised between 0.1 μm and 10 mm.

16. The measurement system according to claim 9, wherein the measurement system is configured to extract of at least one of the following data for examining the condition of the vascular system of a subject:

flow direction of at least a portion of the vascular system, such as a blood vessel or a plurality of blood vessels, pulsation rate, pulsatility index and resistance index of at least a portion of the vascular system, capacitance of wall compliance of at least a portion of the vascular system, inductance of blood flow of at least a portion of the vascular system, pressure of at least a portion of the vascular system, velocity of blood flow in at least a portion of the vascular system, velocity of pulse wave propagation of at least a portion of the vascular system stiffness of at least a portion of the vascular wall.

17. The measurement system according to claim 9, wherein the measurement system is configured to measure the presence of magnetic field originate from magnetic materials or to measure the magnetic properties of small quantity of magnetic materials.

18. The measurement system according to claim 9, wherein the measurement system is configured for non-destructive detection of cracks or thickness reduction in walls containing ferrous compounds or magnetic impurities or containing ferrous compounds and magnetic impurities, such as oil or gas pipelines, oil and gas tankers or any architectures of oil or gas containers.

19. The measurement device according to claim 8, wherein the electromagnetic shielding structure is made of mu-metal or comprises a Faraday cage.

\* \* \* \* \*